United States Patent
Schueth et al.

(10) Patent No.: US 10,906,850 B2
(45) Date of Patent: Feb. 2, 2021

(54) PROCESS FOR THE OLIGOMERIZATION OF ACETYLENE IN THE PRESENCE OF HYDROGEN AND A SOLID CATALYST

(71) Applicant: STUDIENGESELLSCHAFT KOHLE MBH, Muelheim an der Ruhr (DE)

(72) Inventors: Ferdi Schueth, Muelheim an der Ruhr (DE); Ioan-Teodor Trotus, Muelheim an der Ruhr (DE)

(73) Assignee: STUDIENGESELLSCHAFT KOHLE MBH, Mülheim an der Ruhr (DE)

( * ) Notice: Subject to any disclaimer, the term of this patent is extended or adjusted under 35 U.S.C. 154(b) by 0 days.

(21) Appl. No.: 16/307,523

(22) PCT Filed: May 30, 2017

(86) PCT No.: PCT/EP2017/063016
§ 371 (c)(1),
(2) Date: Dec. 6, 2018

(87) PCT Pub. No.: WO2017/211620
PCT Pub. Date: Dec. 14, 2017

(65) Prior Publication Data
US 2019/0256442 A1    Aug. 22, 2019

(30) Foreign Application Priority Data

Jun. 6, 2016 (DE) .......... 10 2016 110 371

(51) Int. Cl.
| | |
|---|---|
| *C07C 2/38* | (2006.01) |
| *B01J 29/14* | (2006.01) |
| *B01J 29/46* | (2006.01) |
| *B01J 29/72* | (2006.01) |
| *B01J 29/85* | (2006.01) |
| *B01J 29/24* | (2006.01) |
| *B01J 37/00* | (2006.01) |
| *B01J 35/02* | (2006.01) |
| *B01J 37/08* | (2006.01) |
| *C07C 11/08* | (2006.01) |
| *C07C 11/167* | (2006.01) |

(52) U.S. Cl.
CPC ............... *C07C 2/38* (2013.01); *B01J 29/14* (2013.01); *B01J 29/146* (2013.01); *B01J 29/24* (2013.01); *B01J 29/46* (2013.01); *B01J 29/7215* (2013.01); *B01J 29/85* (2013.01); *B01J 37/0009* (2013.01); *B01J 35/023* (2013.01); *B01J 37/0036* (2013.01); *B01J 37/08* (2013.01); *B01J 2229/186* (2013.01); *C07C 11/08* (2013.01); *C07C 11/167* (2013.01); *C07C 2523/74* (2013.01); *C07C 2529/14* (2013.01); *C07C 2529/24* (2013.01); *C07C 2529/46* (2013.01); *C07C 2529/74* (2013.01); *C07C 2529/76* (2013.01); *C07C 2529/85* (2013.01)

(58) Field of Classification Search
CPC ... C07C 2/38; C07C 2523/74; C07C 2529/14; C07C 2529/24; C07C 2529/46; C07C 2529/74; C07C 2529/76; C07C 2529/85; C07C 11/08; C07C 11/167; B01J 37/0009; B01J 37/0036; B01J 37/08; B01J 29/14; B01J 29/146; B01J 29/247; B01J 29/46; B01J 29/7215; B01J 29/85; B01J 2229/186; B01J 35/023
See application file for complete search history.

(56) References Cited

U.S. PATENT DOCUMENTS

| | | |
|---|---|---|
| 1,926,056 A | 9/1933 | Nieuwland |
| 2006/0217579 A1 | 9/2006 | Bailey |
| 2007/0292343 A1 | 12/2007 | Chen |
| 2013/0204056 A1 | 8/2013 | Davis et al. |

OTHER PUBLICATIONS

Pereira et al. ("Acetylene Polymerization in a H-ZSM-5 Zeolite". The Journal of Physical Chemistry, vol. 95, No. 2, 1991, 705-709) (Year: 1991).*
Zhivonitko et al. ("Acetylene Oligomerization over Pd Nanoparticles with Controlled Shape: A Parahydrogen-Induced Polarization Study". J. Phys. Chem. C 2016, 120, 4945-4953) (Year: 2016).*
J. Szanyi et al; "Di-and Trimerization of Acetylene over a Model Sn/Pt Catalyst"; J. Am. Chem. Soc. 1995, 117, pp. 1034-1042.
International Search Report and Written Opinion dated Aug. 29, 2017 in corresponding PCT/EP2017/063016.

\* cited by examiner

*Primary Examiner* — Youngsul Jeong
*Assistant Examiner* — Jason Y Chong
(74) *Attorney, Agent, or Firm* — Norris McLaughlin, P.A.

(57) ABSTRACT

The present invention refers to a process for oligomerization of acetylene in the presence of hydrogen and a solid catalyst.

10 Claims, No Drawings

PROCESS FOR THE OLIGOMERIZATION OF ACETYLENE IN THE PRESENCE OF HYDROGEN AND A SOLID CATALYST

This application is a 371 of PCT/EP2017/063016, filed May 30, 2017, which claims foreign priority benefit under 35 U.S.C. § 119 of the German Patent Application No. 10 2016 110 371.3, filed Jun. 6, 2016, the disclosures of which are incorporated herein by reference.

The present invention refers to a process for oligomerization of acetylene in the presence of hydrogen and a solid catalyst.

In the state of the art on acetylene oligomerization with solid catalysts, reports on acetylene oligomerization in the gas phase are very scarce.

Oligomerization reactions of acetylene are not applied on an industrial scale in the present days. The only process for acetylene oligomerization applied industrially in history, known as the Nieuwland process used a copper (I) chloride-potassium chloride slurry to convert acetylene to vinylacetylene and divinylacetylene.

Further studies have been made in the state of art. For example, H-ZSM-5 has been used at temperatures between 250° C. and 500° C. and space velocities between 3900 and 15000 $h^{-1}$ to produce a wide range of aromatics with 6 to 13 carbon atoms. Metal loaded zeolites with Ni, Pd or Pt have also been tested in the reaction of methane and acetylene at 400° C. A wide range of products, most of which have more than 6 carbon atoms, was obtained.

Fluorinated alumina was also studied as a catalyst for acetylene oligomerization. The temperatures used were in the range of 300° to 400 C., space velocities were in the range of 800° to 1200 $h^{-1}$ and products obtained were aliphatics and aromatics in the C1-C15 range.

Nickel supported on a mixture of H-ZSM-5 and alumina can convert acetylene in the presence of a hydrogen donor, like water. The reaction proceeds at 350° to 400 C. at a space velocity around 2100 $h^{-1}$ and produces mostly paraffines.

Nickel supported on silica catalysts, in the presence of hydrogen can oligomerize acetylene at a conversion of nearly 100% at 140° C. using a mixture of 25% acetylene in hydrogen at a space velocity of 5000 $h^{-1}$, with nearly 50% selectivity to alkenes with 4 to 10 carbon atoms, the major side product being ethylene.

For all these reports, the oligomerization reactions proceed with the production of hydrocarbons with both even and odd carbon numbers. Selectivities for butenes are below 20%.

Thus, there is still the need for an oligomerization catalyst which allows production of alkenes, in particular butadiene and butenes, in a higher yield and selectivity.

Generally when working with acetylene, it is recommended not to use copper containing materials when constructing the equipment that comes in contact with acetylene because this is known to produce copper acetylide which is explosive.

The inventors have carried out studies to develop a process for converting acetylene into alkenes. No such process has been described in the literature so far and such process could be an economically attractive process in the future.

As very few publications exist on the topic of acetylene oligomerization over solid catalysts, the inventors started with a screening of supported metal catalysts. The tests revealed that nearly all of the tested metals such as Cr, Mn, Fe, Co, Ni, Zn, Au, Pd, Pt, Mo, W, Nb, Re were less suitable than copper containing catalysts. The inventors found out that such a copper catalyst supported on a solid carrier was active and selective for the production of even numbered hydrocarbons. The inventors decided to use a copper catalyst though it is known that when working with acetylene, it is generally recommended not to use copper containing materials as discussed above. The more surprising it is for the inventors that the inventive catalyst can be used without any harm and leads to the highest yield and selectivity observed so far for the desired products.

In the context of this invention, the term "molecular sieve" refers to any crystalline material, regardless of chemical composition, with pore sizes of molecular dimensions (<2 nm). The term refers solely to the property of these materials to selectively separate molecules based on size exclusion principles.

The term "ion-exchanging material" refers to any solid material which presents the property of ion exchange. This property manifests itself when the material comes in contact with an electrolyte solution and consists in an adsorption of electrolytes from the solution on the surface of the material accompanied by a simultaneous desorption of electrolytes from the surface of the material into the solution. Depending on the charge of the electrolytes two types of ion-exchange are possible: "cation-exchange" and "anion-exchange". Thus "cation-exchanging materials" can exchange positive ions and "anion-exchanging materials" can exchange negative anions.

The term oligomerization refers to a process where reactions occur in which the coupling of smaller molecules occurs leading to the formation of larger molecules. In order for a process to constitute an oligomerization process at least 50% of the reactions occurring should result in the formation of larger molecules from smaller ones. In the concrete context of acetylene oligomerization which constitutes the object of the current invention, a process is envisioned where less than 50% of acetylene is hydrogenated to ethylene or ethane, and more than 50% of the acetylene is coupled to form molecules with 4, 6, 8, 10, etc. carbon atoms.

The first catalysts tested by the inventors were comprised of supported metal particles and they produced a significant amount of heavy oligomers which lead to the clogging of the catalyst bed. The inventors then found out that confining the copper into a microporous material improved the catalysis results. The inventors preferably used cation-exchanging alumino-silicates and the alumino-silicate that performed best was zeolite Y with a Si/Al ratio of 2.55. However, the conversion results greatly depend on the reaction conditions and the inventors developed a controlled catalyst activation procedure as described below and in the experimental details.

Thus, the inventors have developed a new process for generating an active catalyst; and a process for making use of said catalyst for oligomerizing acetylene leading to unprecedented yields of butenes and butadiene from acetylene.

The essential aspect of this invention is the use of copper to facilitate the reaction of acetylene and hydrogen to produce the desired butenes and butadiene along with other even numbered hydrocarbons. Any material which contains copper either as particles deposited on a support, or atomically dispersed as is the case in copper exchanged zeolites, will perform this reaction to some extent under the given condition.

Therefore, the present invention is generally directed to the use of copper containing materials with acetylene and hydrogen at 20-700° C. to produce oligomers and hydrogenated oligomers of acetylene In the sense of the invention, "copper containing material" or "copper containing support" is intended to mean copper in any oxidation state, that is copper (0) particles of size below 1 μm, copper (I) and/or copper (II) ions. Said copper in any oxidation state may be loaded onto the support by applying an aqueous copper salt solution which copper salt may be reduced to copper (0) particles.

Preferably the material for this use contains atomically dispersed copper as obtainable with cation exchange materials.

Preferably, the copper alumino silicate is a copper loaded Zeolite Y which can be prepared as described in the experimental part.

The invention is further directed to a process for oligomerization of acetylene, wherein acetylene is treated with a protective gas-hydrogen mixture in the presence of the copper loaded support material, preferably a copper loaded alumino silicate, at elevated temperatures in the range of 200-250° C. and at an operating pressure of 2-20 bar, whereby the hydrogen to acetylene molar ratio is between 3 and 5.

In more detail, the present invention comprises a:
A process for oligomerizing acetylene in the presence of a catalyst, said process comprising the step of reacting acetylene and hydrogen in an inert gas in a gas phase reactor in the presence of a copper containing support selected from molecular sieves, amorphous aluminosilicates, zeolites, clays, metal oxides, metal phosphates, cation exchange materials at an elevated temperature in the range of 20 to 700° C., preferably 100° to 700° C., more preferably 180° to 300° C., and at a reaction pressure of up to 35 bar, preferably 2 to 20 bar;

a process as mentioned before, wherein the copper containing support is selected from the group consisting of cation exchange materials with a content of 0.01 to 20 wt. % Cu in the cation exchange material;

a process as mentioned before, wherein the cation-exchange material is a molecular sieve;

a process as mentioned before, wherein the molecular sieve is a alumo silicate preferably selected from zeolites including faujasite, mordenite, ZSM-5, zeolite β and SAPO-34;

a process as mentioned before, wherein the cation exchange material is an alumo silicate with an $SiO_2/Al_2O_3$ ratio between 2 and 1000, preferably 2 and 100, more preferably between 3 and 40 and most preferably between 4 and 20;

a process as mentioned before, wherein the reaction gas comprises the inert gas and hydrogen in a ratio of between 0.1% and 99.9 vol.-% $H_2$ in the inert gas, the partial pressure of acetylene is between 0.01 and 10 bar, preferably between 1 and 35% of total pressure in the gas phase and the molar ratio of the flow of acetylene per minute to the copper amount in the material used is between 0.01 and 100, preferably between 0.1 and 30;

a process as mentioned before, wherein the catalyst is used in an activated form which catalyst has been activated at conditions of lower reaction pressure, and lower amounts of reacting compounds and of the catalyst, compared to the reaction conditions after activation;

a process as mentioned before, wherein the process includes the step of activating the catalyst in the gas phase reactor before the continuous process for oligomerizing the acetylene is started, and the use of a copper containing support selected from amorphous aluminosilicates, molecular sieves, zeolites, clays, metal oxides, metal phosphates, cation-exchange materials as a catalyst for oligomerizing acetylene.

In the inventive process, the protective gas such as nitrogen serves only to dilute the acetylene-hydrogen mixture and the protective gas can constitute 0.1% to 99.9% volume percent of the gas phase. If not otherwise indicated, the percentages of the gases refer to vol.-%.

With the present invention, it is possible that using a copper containing solid allows the formation of predominantly even numbered hydrocarbons. Furthermore, selectivities to butenes in the range of 30-55% can be reached depending on activating conditions and on reaction conditions.

Thus, the present invention provides a method for converting acetylene to butenes with yields of 20-55%, better than any other system reported in literature so far.

When carrying out the process of the present invention, the first contact of acetylene with catalyst must be very precisely controlled (temperature, acetylene partial pressure, heat transfer ability of the catalyst bed, catalyst bed shape) as these will determine the catalytic properties of the system.

At low temperatures (<200° C.) contact with acetylene might result in an inactive catalyst, depending on the specific conditions.

At medium temperatures (200-250° C.) a high concentration of acetylene can cause the catalyst to glow red upon contact inducing the formation of a very active catalyst (around 5 g acetylene converted per hour by one gram of catalyst). If the catalyst bed is too long formation of other hydrocarbons at the contact of acetylene with the top of the catalyst bed can lead to the formation of less active phases in the bottom of the bed, as this part of the catalyst bed does not have the opportunity to react with the same acetylene concentration as the top of the bed in order to form the active phase. Thus, the skilled man has to balance the conditions concerning temperature, amounts and ratios of the reacting components and the reactor conditions and will find the best performance for each situation.

At high temperatures, a low concentration of acetylene with a short bed length suffices to form a highly active catalyst (~3.5 g acetylene converted per hour by one gram of catalyst).

In the inventive process, given the elevated pressure of the process and the potentially large dead volume of the flow setup used, it might be difficult to accurately control the concentration of acetylene in the gas phase at the moment when the catalyst is contacted by acetylene for the first time. Therefore it is advisable to perform the activation of the catalyst in a separate unit which allows a more rigorous control of process conditions when acetylene first contacts the catalyst than is possible with a high pressure flow setup, in order to ensure an optimal control of the process in terms of activity, selectivity and catalyst stability.

In order to ensure a homogeneous activation, the catalyst bed must have a short length, activation temperatures which may preferably be higher than the normal reaction temperature are required and also a very dilute flow of acetylene can be beneficial in order to avoid local hotspot formation when the acetylene contacts the catalyst.

GENERAL PROCEDURE FOR THE CATALYST PREPARATION MATERIAL PREPARATION

For the catalyst used in the process of the present invention, cation exchange materials such as amorphous alumino silicates, zeolites, clays etc. may be used, preferably molecular-sieve type cation exchange materials such as zeolites (faujasite, mordenite, ZSM-5, zeolite β, SAPO-34 etc.). Of particular preference are alumino silicates with a $SiO_2/Al_2O_3$ ratio between 2 and 1000, preferably the $SiO_2/Al_2O_3$ ratio is between 4 and 100. Between 0.01 and 5 weight % of said ion exchange material C-M, where C is the cation initially compensating the charges on the framework of the ion exchange material M, as for C exemplified by $Na^+$, $NH_4^+$, $Cs^+$, $K^+$, $Rb^+$, $H^+$, $Ca^{2+}$ etc. may be used for preparing the Cu— ion loaded material by dispersing the material C-M in a solution containing $Cu^{2+}$ with a preferred concentration between 0.05 and 350 g/L $Cu^{2+}$. Stirring is generally carried out at temperature between 20-120° C. for a minimum of 0.5 hours, the Cu-M material is filtered and washed with 0.1 to 10 L water per gram of C-M used at the start.

The ion exchange of the C-M material with Cu does not have to be complete, the metal C can still be present in the final material, compensating from 0.01 to 99.9% of the ion exchange capacity, and the procedure can be repeated multiple times to increase copper loading. Finally, the $Cu^{2+}$ loaded material is dried at below <100° C. for sufficient time, generally from 5-60 hours, in static air in order to have a smooth drying process.

Alternatively procedures like the one reported in US20150110711 where the copper is encapsulated into the molecular sieve during the synthesis can also be applied.

Preferably, the dried material is used for preparing the final catalyst body to best satisfy heat/mass transfer, taking also the reactor shape into consideration.

Material Activation

The Cu-M loaded material prepared as described above is placed inside a tubular reactor with adjustable flow and composition of a gaseous mixture through the tube. The activation conditions have to be adapted to the specific material and reactor conditions and may be as follows:

Temperature between 20 and 700° C. (most preferably 180-300° C.)
Pressure >0 to 35 bar
Gas phase an inert gas such as $N_2+H_2$ between 0.1% and 99.9% $H_2$ in $N_2$
Controlled flow with a partial pressure of acetylene between 0.01 and 10 bar, preferably between 1 and 35% of total pressure
Controlled introduction of acetylene in an amount of between 0.1 and 100 times the copper amount in the Cu-loaded material used, preferably between 1 and 30, into the gas flow after 0.01 to 24 h, preferably 0.1 to 3 h after the activation temperature is reached.

The inventors have found out that the conditions, especially the partial pressure of acetylene and the acetylene/copper ratio, during activation severely affect the performance of the catalyst. Thus, the activation step is of outmost importance to obtain an active catalyst for acetylene oligomerization and to obtain reproducible activity. When carrying out the activation step, the skilled man can work inside the borders of the process parameters as defined before and he will be able to adapt the activation to the actual conditions.

Process Parameters

The Cu loaded material prepared and activated as described before is placed into a reactor, such as a tubular reactor, which is equipped with means for adjusting flow and composition of a gaseous mixture through the reactor. The temperature is adjusted to 20° and 700° C., most preferably 180-300° C., and the gas pressure is adjusted to >0 to 35 bar, preferably 2 to 20 bar. The gas phase is introduced as $N_2+H_2+C_2H_2$ in a composition of between 0.1% and 99.9% $N_2$ (Ar, He and other inert gases or mixtures thereof are also useful) and the rest $H_2/C_2H_2$ with a ratio between 1 and 10, preferably between 2 and 8. The molar ratio of the amount of $C_2H_2$ introduced per minute to the amount of copper contained in catalyst (in moles) might be between 0.01 and 100, preferably between 0.1 and 50, and more preferably between 0.5 and 10. In a different embodiment, the molar ratio of the amount of $C_2H_2$ introduced per minute to the amount of copper contained in catalyst might be between 0.1 and 100, preferably between 3 and 30.

The process conditions are similar to the activation conditions. If the flow of acetylene on the catalyst during the first minutes and especially during the first seconds of the contact can be accurately controlled very active catalysts can be obtained reproducibly without the separate activation step.

EXPERIMENTAL PART

Preparation Examples

Example 1

7.2 g Copper nitrate trihydrate is dissolved in 120 g distilled water at room temperature. After complete dissolution of the solid a clear blue solution is obtained. To this 3 g Zeolite Y (Si/Al ratio 2.55) in sodium form (Na—Y) are added. The obtained suspension is then refluxed at 90-110° C. for 15-25 hours. Afterwards the suspension is filtered and the obtained solid is washed with 1-4 liters of distilled water. The washed solid is then dried for 15-25 hours at 90° C. in a static air oven.

Example 2

1 g Copper (II) acetate monohydrate is dissolved in 500 g distilled water at room temperature. After complete dissolution of the solid a clear blue solution is obtained. To this 3 g Na—Y (Si/Al ratio 2.55) are added. The obtained suspension is then stirred at room temperature for 0.5-25 hours. Afterwards the suspension is filtered and the obtained solid is washed with 1-4 liters of distilled water. The washed solid is then dried for 15-25 hours at 90° C. in a static air oven.

Example 3

0.2 g Copper (II) acetate monohydrate is dissolved in 100 g distilled water at room temperature. After complete dissolution of the solid a clear blue solution is obtained. To this 3 g Na—Y (Si/Al ratio 2.55) are added. The obtained suspension is then stirred at room temperature for 15-25 hours. Afterwards the suspension is filtered and the obtained solid is washed with 1-4 liters of distilled water. The washed solid is then dried for 15-25 hours at 90° C. in a static air oven.

According to the inventors, it is essential in all cases that the drying is performed under a static atmosphere, at a temperature below the boiling point of water, to avoid the fast evaporation of water which can perturb the structure of the material.

The dried catalyst is pelletized using a hydraulic press and the pellets are subsequently crushed and sieved. The fraction of particles measuring between 3-400 μm is used for catalytic testing. This particle size works well for the research-scale reactor, but other particle sizes might work better for other dimensions of the reactor and at different space velocities.

The materials obtained from this process have generally the following elemental composition in weight percent of the final product:
20-30% Si;
10-12% Al;
0.01-16% Cu;
0.5-13% Na,
5-25% water (rest is oxygen)

Following similar protocols, any soluble Copper (II) salt could produce active catalysts upon ion-exchange with Na—Y. Other alumino-silicates with ion-exchange capabilities can also be loaded with copper (I) and/or (II) by procedures similar to those described above. These procedures can also lead to active materials for acetylene oligomerization.

Additionally it must be noted that under the conditions of the inventive process or of the inventive catalyst activation procedure the copper can be partially or completely reduced to copper (I). In consequence, materials prepared via ion-exchange techniques which allow the use of copper (I) salts such as vapor phase ion exchange of a protonated zeolite such as H—Y with a volatile copper salt such as copper (I) chloride can also lead to active materials for acetylene oligomerization.

Example 4

Preparation of amorphous ion-exchanging silica-alumina was based on a state of art procedure (Applied Catalysis A: General 388, 68-76 (2010)) 26 g of tetraethylorthosilicate (TEOS) are stirred in 30 mL of ethanol for 30 min. A solution of 3.685 g malic acid in 22.5 g $H_2O$ is prepared and added dropwise over 20 min to the TEOS solution. 12.08 g Al-secbutoxide are added to 27.5 g ethanol and stirred until this solution becomes clear. Afterwards this solution is added dropwise over 20 min to the TEOS solution. After mixing for one hour, the temperature of the solution is raised to 60° C. and maintained at this value until complete gelation, which will become apparent because the magnetic stirrer becomes stuck. This step will most likely take more than one day. After gelation is observed in the whole volume of the solution, the gel is aged for another day at 60° C. Afterwards the gel is calcined in a static air atmosphere in a box furnace by heating to 600° C. with a ramp of 2.4° C. per minute and holding the temperature at 600° C. for 12 h.

The ion exchange of the obtained amorphous silica-alumina is performed in a manner identical to that used for zeolite Y.

7.2 g Copper nitrate trihydrate is dissolved in 120 g distilled water at room temperature. After complete dissolution of the solid a clear blue solution is obtained. To this solution 3 g of the amorphous silica alumina are added. The obtained suspension is then refluxed at 90-110° C. for 15-25 hours. Afterwards the suspension is filtered and the obtained solid is washed with 1-4 liters of distilled water. The washed solid is then dried for 15-25 hours at 90° C. in a static air oven. The ion exchange procedure, although identical to the one that gave a material with 9-10 wt. % Cu when applied to zeolite Y, only results in a material with 1-2 wt. % Cu. This is due to the fact that for the zeolite theoretically all aluminum atoms result in the formation of ion exchange sites, whereas for the amorphous material this is not the case.

Example 5

Cu-SAPO-34 was synthesized by direct incorporation of a polyamine copper complex, according to patented procedures (US20150110711), using diethylamine as organic structure directing agent. A synthesis gel of the following molar composition: 0.81 DEA: 1 Al: 0.2 Si: 0.8 P: 18 $H_2O$: 0.09 Cu: 0.09 TEPA, was prepared employing diethylamine, colloidal $SiO_2$ suspension LUDOX® AS-40 (Aldrich), commercial high-purity nanosized dispersible pseudo-boehmite (Disperal, Sasol Materials), a freshly prepared 85 wt. % $H_3PO_4$ aqueous solution, a saturated $CuSO_4$ aqueous solution and tetraethylenepentamine as reagents. In addition, a 5 wt. % (with respect to the nominal mass of silicoaluminophosphate solid) was added as seeds to direct the crystallization of SAPO-34. The gel was treated in PTFE-lined autoclaves at 150° C. for 5 days under static conditions. The resulting solid was then recovered by centrifugation, washed with deionized water 4 times, dried at 90° C. for 12 h and calcined in air flow at 550° C. for 4 hours.

Protocol for Starting a Catalytic Test 0.05 to 2 g catalyst particles with a defined particle size prepared as described above are mixed with silicon carbide which serves as inert material to improve heat transfer from the catalyst bed. A mixture of catalyst+Silicon carbide with a total volume of 0.5 to 20 mL is placed in a stainless steel tubular reactor set at a pressure lower or equal to the operating pressure and heated within 20-40 minutes to 20-400° C. and held at this temperature for 0.01-24 h under a nitrogen and/or hydrogen flow of 50-500 mL/min. During this heating step, activation of the catalyst may be incorporated by the controlled introduction of acetylene in an amount of between 0.1 and 100 times the copper amount in the Cu-loaded material used, preferably between 1 and 30, into the gas flow after 0.01 to 24 h, preferably 0.1 to 3 h after the desired temperature is reached. Otherwise the activation can be performed in a separate step as described in the next section.

Afterwards the reactor is brought to the reaction temperature of 200-250° C. and pressurized to the operating pressure (2-20 bar) with a nitrogen-hydrogen mixture. After a stable pressure is reached, acetylene is allowed to flow over the catalyst. The molar ratio of the amount of $C_2H_2$ introduced per minute to the amount of copper contained in catalyst (in moles) might be between 0.01 and 100, preferably between 0.1 and 50, and more preferably between 0.5 and 10. Under reaction conditions the hydrogen to acetylene molar ratio is between 3 and 5. Nitrogen serves only to dilute the acetylene-hydrogen mixture and nitrogen can constitute 0.1-99.9% volume percent of the gas phase.

The gas mixture leaving the reactor is analyzed via gas chromatography.

Activities observed range between 0.1 and 8 g acetylene converted per gram catalyst per hour. Butene selectivities between 20 and 55% are observed.

Catalyst Activation Procedure

Example 1

0.2 g of copper exchanged Y zeolite material are placed in a quartz tube (20 mm inner diameter) and heated at 400° C.

under a flow of 40 L/h $N_2$ and 15 L/h $H_2$. After the reaction temperature is reached, acetylene is introduced at a flow rate of 0.12 L/h for 3 minutes.

The amount of acetylene in moles flown over the material in this way is roughly 5-20 times the number of moles of Cu contained in the material. The intention is to bring as much as possible of the copper into the active state while avoiding carbon deposition on the catalyst from acetylene decomposition at high temperature.

After this activation step the catalyst is transferred into the high pressure stainless steel reactor and the reaction is performed as described above, omitting the step where the catalyst is first heated under nitrogen and/or hydrogen to 20-400° C. This procedure yields a material which converts 0.5-5 g of acetylene per gram of catalyst per hour with a total selectivity of 30-50% to butenes and butadiene.

Example 2

0.2 g of copper exchanged Y-zeolite are mixed with SiC to give a total volume of particles of 0.7 mL and this mixture is placed in a glass tube (4 mm inner diameter) and heated at 220° C. under a flow of 280 mL/min $N_2$ and 140 mL/m in $H_2$. After the reaction temperature is reached, acetylene is introduced in an amount equal to 3 times the Cu amount contained in the material over a period of 5 to 60 seconds. The material is then transferred into a steel reactor and the catalytic test is started as described above omitting the step where the catalyst is first heated under nitrogen and/or hydrogen to 20-400° C. This procedure yields a material which converts 2-3 g of acetylene per gram of catalyst per hour with a total selectivity of 35-45% to butenes and butadiene.

Example 3

0.25 g of Cu-SAPO-34 prepared as in example 5 for catalyst preparation are mixed with SiC to give a total volume of particles of 0.7 mL and this mixture is placed in a glass tube (4 mm inner diameter) and heated at 220° C. under a flow of 280 mL/min $N_2$ and 140 mL/m in $H_2$. After the reaction temperature is reached, acetylene is introduced in an amount equal to 3 times the Cu amount contained in the material over a period of 5 to 60 seconds.

The material is then transferred into a steel reactor and the catalytic test is started as described above omitting the step where the catalyst is first heated under nitrogen and/or hydrogen to 20-400° C. This procedure yields a material which converts 1.5-2.5 g of acetylene per gram of catalyst per hour with a total selectivity of 30-40% to butenes and butadiene.

The invention claimed is:

1. A process for oligomerizing acetylene in the presence of a catalyst, said process comprising oligomerizing acetylene by reacting a gas phase comprising acetylene, hydrogen and an inert gas in a gas phase reactor in the presence of the catalyst at an elevated temperature of 20° C. to 700° C. and at a reaction pressure of up to 35 bar, wherein the catalyst is a copper containing support selected from the group consisting of molecular sieves, amorphous aluminosilicates, zeolites, clays, metal oxides, metal phosphates, and cation exchange materials.

2. The process according to claim 1, wherein the copper containing support is selected from the group consisting of cation exchange materials with a content of 0.01 to 20 wt. % Cu in the cation exchange material.

3. The process according to claim 1, wherein the cation exchange material is a molecular sieve.

4. The process according to claim 3, wherein the molecular sieve is an alumo silicate.

5. The process according to claim 1, wherein the cation exchange material is an alumo silicate with an $SiO_2/Al_2O_3$ ratio between 2 and 1000.

6. The process according to claim 1, wherein the gas phase comprises the inert gas and hydrogen in a ratio of between 0.1% and 99.9 vol.-% $H_2$ in the inert gas, a partial pressure of acetylene is between 0.01 and 10 bar in the gas phase, and a molar ratio of acetylene flow per minute to an amount of copper (I) and/or copper (II) in the catalyst is between 0.01 and 100.

7. The process according to claim 1, wherein the catalyst is in an activated form and the catalyst has been activated at conditions of lower reaction pressure, and of lower amounts of reacting compounds and of the catalyst, compared to reaction conditions after activation.

8. The process according to claim 7, wherein the reacting acetylene and hydrogen is continuous and the process additionally comprises activating the catalyst in the gas phase reactor before the reacting acetylene and hydrogen is started.

9. The process according to claim 1, wherein the catalyst is a copper containing support selected from the group consisting of amorphous aluminosilicates, zeolites, and clays.

10. The process according to claim 9, wherein the catalyst has been cation-exchanged with $Cu^{2+}$.

* * * * *